(12) United States Patent
Mendlewicz et al.

(10) Patent No.: US 7,662,805 B2
(45) Date of Patent: Feb. 16, 2010

(54) ORAL ANTIDEPRESSANT FORMULATION

(76) Inventors: Julien Mendlewicz, Zonnebloemlaan 4, Dworp (BE) B-1653; Philippe Kriwin, Drève des Renards 83, Brussels (BE) B-1180; Roland Powis De Tenbossche, Leiweg 41, Eppegem (BE) B-1980

( * ) Notice: Subject to any disclaimer, the term of this patent is extended or adjusted under 35 U.S.C. 154(b) by 0 days.

(21) Appl. No.: 11/003,780

(22) Filed: Dec. 6, 2004

(65) Prior Publication Data

US 2005/0085450 A1    Apr. 21, 2005

Related U.S. Application Data

(63) Continuation-in-part of application No. PCT/BE03/00181, filed on Oct. 29, 2003, and a continuation-in-part of application No. PCT/BE03/00078, filed on Apr. 30, 2003.

(30) Foreign Application Priority Data

Jun. 10, 2002    (WO) .................... PCT/BE02/00094

(51) Int. Cl.
| A61K 31/60 | (2006.01) |
| A61K 31/135 | (2006.01) |
| A01N 33/02 | (2006.01) |
| C07D 307/87 | (2006.01) |
| C07D 307/93 | (2006.01) |
| C07C 211/00 | (2006.01) |

(52) U.S. Cl. .................. 514/165; 514/649; 514/651; 514/647; 549/462; 564/428; 564/308

(58) Field of Classification Search ................ 514/165, 514/716, 649, 651, 647; 549/462, 428, 308
See application file for complete search history.

(56) References Cited

U.S. PATENT DOCUMENTS

| 4,594,358 A | | 6/1986 | Hynes | |
| 4,650,789 A | * | 3/1987 | Pollack | 514/23 |
| 4,866,046 A | * | 9/1989 | Amer | 514/159 |
| 5,648,396 A | * | 7/1997 | Young et al. | 514/651 |
| 6,245,782 B1 | | 6/2001 | Serebruany et al. | |
| 6,432,989 B1 | | 8/2002 | Chen | |
| 6,440,457 B1 | * | 8/2002 | Edgren et al. | 424/468 |

FOREIGN PATENT DOCUMENTS

| EP | 0 193 355 | 9/1986 |
| EP | 0 193 355 A2 | 9/1986 |
| GB | 2 287 404 | 9/1995 |
| WO | WO 98 50044 | 11/1998 |
| WO | WO 98/50044 A1 | 11/1998 |
| WO | WO 00/28980 | 5/2000 |
| WO | WO 00 59489 | 10/2000 |
| WO | WO 03/103643 | 12/2003 |

OTHER PUBLICATIONS

Shad, M. U.; Harvey, A. T.; Lucot, J. B. J. Clin. Psychiatry 1997, 58, 549-550.*
Juárez-Olguín, H.; Jung-Cook, H.; Flores-Pérez, J.; Lares-Asseff, I. Neuropsychopharmacology 2000, 22, 100-101.*
Sauer et al. (Circulation, Oct. 16, 2001, p. 1894-98).*
Sist (J of Pain Symptom Management, vol. 15, Jun. 6, 1998).*
Zoloft((http://media.pfizer.com/files/products/uspi_zoloft.pdf#page=43).*
MeRec Briefing, "The Management of Depression in Primary Care".*
Clinical Pharmacology of SSRI document (p. 1-10).*
"A Blind Panic", J. Ayuk et al., The Lancet, Lancet Limited, London, GB. vol. 357, No. 9264, Apr. 21, 2001, p. 1262.
"Severe Bleeding Associated with use of Low Molecular Weight Heparin and Selective Seratonin Reuptake Inhibitors", American Journal of Medicine, vol. 113, No. 6, Oct. 15, 2002, pp. 530-532.
"Adverse Effects of Imipramine are Increased by Interaction with ASA in Depressed Patients", Neuropsychopharmacology, vol. 22, No. 1, Jan. 2000, pp. 100-101.
"Association Between Selective Serotonin Reuptake Inhibitors and Upper Gastrointestinal Bleeding: Population Based Case-Control Study", BMJ, vol. 319, No. 7217, Oct. 23, 1999, pp. 11-6-1109.

* cited by examiner

Primary Examiner—Sreeni Padmanabhan
Assistant Examiner—Umamaheswari Ramachandran
(74) Attorney, Agent, or Firm—Sughrue Mion, PLLC

(57) ABSTRACT

Oral antidepressant formulation comprising an effective antidepressant amount of at least one pharmaceutically acceptable antidepressant active agent and an effective amount lower than 50 mg of acetylsalicylic acid, derivatives of acetylsalicylic acid, or diaspirin, for reducing the onset of antidepressant action.

46 Claims, No Drawings

ORAL ANTIDEPRESSANT FORMULATION

RELATED APPLICATIONS

This application is a continuation in part of PCT/BE 03/00078 filed on Apr. 30, 2003, published on Dec. 18, 2003 under number WO 03/103643, and claiming the priority of PCT/BE02/00094 filed on Jun. 10, 2002, as well as a continuation in part of PCT/BE 03/00181 filed on Oct. 29, 2003 published on May 6, 2005 under number WO2005/039545.

FIELD OF THE INVENTION

The present invention relates to a formulation and a method for reducing the time of onset of antidepressant action of pharmaceutically acceptable antidepressant active agents selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

THE PRIOR ART

Antidepressant formulations are well known. Said formulations (marketed or in development) comprise a pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists and NK3 (neurokinin) antagonists.

The major problem of human antidepressant is the onset time required for obtaining an antidepressant action, said onset time being often greater than 4 weeks. This means a great risk that the patient decides him self to stop the treatment in view of the lack of action after two weeks treatment, or to take a too large dose, possibly a toxic dose, of one or more antidepressant agents.

Another problem of antidepressant formulations is that they are inefficient for some patients (not responding patients) for reason not yet known.

DESCRIPTION OF THE INVENTION

The present invention has for object an oral antidepressant formulation with a reduced time of onset of antidepressant action. It has been discovered that by using specific compound(s), it was possible to reduce the onset time of antidepressant action of pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

The invention relates also to an oral antidepressant formulation efficient for at least 50% (preferably at least 70%, most preferably more than 80%) of the SSRI not responding patients, advantageously for at least 50% (preferably at least 70%, most preferably more than 80%) of the patients not responding to a pharmaceutically acceptable antidepressant active agent taken alone at a dose of less than 20 mg, said pharmaceutically acceptable antidepressant active agent being selected from the group consisting of SNRIs (serotonin noradrenaline reuptake inhibitors), CRF (corticotropic releasing factor) antagonists, NK1 (neurokinin) antagonists, NK2 (neurokinin) antagonists and NK3 (neurokinin) antagonists. It has been discovered that by using specific compound(s), it was possible to render therapeutically active pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, for patients or humans not responding to antidepressant taken alone, such as SSRI taken alone.

By antidepressant agent, it is meant in the present specification the antidepressant agent as in its free base form as well as in a pharmaceutically acceptable acid addition salt form (for example salt of (O)—N-methyl-3-phenyl-3-[($\alpha$-$\alpha$-$\alpha$-trifluoro-p-tolyl)oxy] propylamine in case of fluoxetine).

Such acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono- and dicarboxylates, phenyl-substituted alkanoates, hydroxy alkanoates and alkanedioates, aromatic acids, aliphatic and aromatic sulfonic acids, etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 8-hydroxybutyrate, glycolate, malate, tartrate, methanesulfonate, propanesulfonates, naphthalene-1-sulfonate, naphthalene-2-sulfonate, mandelate and the like salts.

The invention relates to an oral antidepressant formulation comprising an effective antidepressant amount of one or more pharmaceutically acceptable antidepressant active agents selected from the group consisting of selective serotonin reuptake inhibitors (SSRI), SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof (most preferably SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof), and an effective amount of at least a compound or additive selected from the group consisting of acetylsalicylic acid (ASA), salts thereof, ester thereof, the acid form being however preferred, diaspirin and mixtures thereof, for reducing the onset time of antidepressant action of the pharmaceutically acceptable antidepressant active agents selected from the group consisting of selective serotonin reuptake inhibitor(s), SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. ASA, salts and esters thereof, and mixtures thereof are however the preferred compound(s) to be combined with the pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

Advantageously, the amount of aspirin, diaspirin or salts and esters of acetylsalicylic acid, and combinations thereof is lower than 50 mg, preferably lower than 40 mg, such as comprised between 5 and 35 mg.

While the mechanism of action is not clear, it seems that the reduced onset or the efficiency of the antidepressant for patient (human) not responding to SSRI taken alone at dose of less than 20 mg is due to one or more of the following reasons:
 better passage of the antidepressant active agent in the blood
 higher fluidity of the blood
 increased deposit in the brain
 activation of the brain or specific sites thereof, so that the brain or some specific sites have a higher receptivity for the antidepressant active agent One or more other advantages of the formulation of the invention are:
 quicker action
 less headaches
 possibility to reduce the doses of antidepressant
 less risk factor for suicide (for example due to the immediate action of the antidepressant)
 efficient for SSRI not responding patients
 etc.

The formulation comprises advantageously an effective amount of at least a compound selected from the group consisting of acetylsalicylic acid, salts and esters of acetylsalicylic acid, and mixtures thereof, for reducing at least 15%, advantageously at least 20%, preferably at least 50% the average onset of action of the pharmaceutically acceptable antidepressant active agents selected from the group consisting of SSRI, SNRIs (serotonin noradrenaline reuptake inhibitors), CRF (corticotropic releasing factor) antagonists, NK1 antagonists, NK2 antagonists, NK3 antagonists and combinations thereof, most preferably from the group consisting of SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. Preferably, the effective amount of one or more compounds (selected from the group consisting of aspirin, salts thereof, esters thereof, diaspirin and combinations thereof) for reducing the onset time of action of the pharmaceutically acceptable antidepressant active agents selected from the group consisting of SSRI, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof is lower than 5 times the amount of pharmaceutically acceptable antidepressant active agents selected from the group consisting of SSRI, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. Most preferably, the effective amount of one or more compounds (selected from the group consisting of aspirin, salts thereof, esters thereof, diaspirin and combinations thereof) for reducing the onset time of action of pharmaceutically acceptable antidepressant active agents selected from the group consisting of SSRI, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof is lower than 2 times, advantageously lower than 1.5 times, preferably lower than 1 times the amount of pharmaceutically acceptable antidepressant active agents selected from the group consisting of SSRI, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

According to a preferred embodiment, the formulation comprises a quick release effective amount of at least a compound selected from the group consisting of acetylsalicylic acid, salts and esters of acetylsalicylic acid, diaspirin, and mixtures thereof, for reducing the onset of action of the selective serotonin reuptake inhibitor(s).

According to a detail of a specific embodiment, the formulation comprises particles, core, microparticles, spherical particles comprising at least one pharmaceutically acceptable antidepressant active agent selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, and possibly at least a compound selected from the group consisting of acetylsalicylic acid, salts and esters of acetylsalicylic acid, and mixtures thereof, said particles, core, microparticles, spherical particles being advantageously provided with a coating comprising at least a compound selected from the group consisting of acetylsalicylic acid, salts and esters of acetylsalicylic acid, diaspirin, and mixtures thereof, for reducing the onset time of action of the pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, said coating being substantially free of pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. The coating is for example made by using a water soluble polymer. It has however to be noted that in case the SSRI and the additive selected from the group consisting of acetylsalicylic acid, salts and esters of acetylsalicylic acid, and mixtures thereof, are mixed together so as to prepare matrix comprising both compounds, the additive acts as means for ensuring a better dissolution of the pharmaceutically acceptable antidepressant active agents selected from the group consisting of SSRI, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, possibly mixed with SSRI and/or a better passage in the organism. It can be advantageous to provide a barrier coating between the SSRI containing core, particles, etc. and the coating containing the additive, so as to avoid any interaction between the pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, and the additive. Such a barrier coating is for example a water insoluble coating (polymer, etc.). This is advantageous for avoiding any stability problem.

Advantageously, the composition of the invention comprises a pharmaceutically acceptable antidepressant active agent selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, the SSRI (selective serotonin reuptake inhibitor) being most preferably selected from the group consisting of citalopram, especially escitalopram or the s-isomer of citalopram, paroxetine, sertraline, fluvoxamine, fluoxetine. Fluoxetine, citalopram, escitalopram and sertraline are the most preferred SSRI.

While the formulation can be liquid, the formulation is advantageously solid. Solid formulation means a formulation which has a solid aspect, even if the pharmaceutically acceptable antidepressant active agent selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof is in a liquid or semi liquid form in a carrier or on a carrier. For example, the solid form comprises from 4 mg up to 100 mg, preferably from 4 to 20 mg of pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

The invention relates further to an antidepressant system comprising at least a formulation, advantageously an oral formulation, with an effective antidepressant amount of one or more pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, and at least a formulation, advantageously an oral formulation, with an effective amount of at least a compound selected from the group consisting of acetylsalicylic acid, salts and esters of acetylsalicylic acid, diaspirin, and mixtures thereof, for reducing the onset of action of pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. The two formulations can be administered simultaneously or successively, and/or with different administration pathways (oral, rectal, parenteral, etc.) or with the same administration pathways. The system of the invention has advantageously one or more characteristics of the oral formulation of the invention as described here above.

The invention relates also to an oral antidepressant formulation for human comprising an effective antidepressant amount of at least one pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, and an effective amount of at least one compound selected from the group consisting of acetylsalicylic acid, salts and esters of acetylsalicylic acid, diaspirin, and mixtures thereof, for reducing the onset time of action of the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, whereby said formulation comprises a means for controlling the release of the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, with respect to the release of the compound selected from the group consisting of acetylsalicylic acid, salts and esters of acetylsalicylic acid, diaspirin, and mixtures thereof. Advantageously, the formulation comprises a means for delaying the start of release of the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, from 3 minutes to 60 minutes, preferably from 5 minutes to 45 minutes, most preferably from 7 minutes to 30 minutes, with respect to the release of at least 50% by weight (advantageously at least 75% by weight, preferably at least 85% by weight) of the compound selected from the group consisting of acetylsalicylic acid, salts and esters of acetylsalicylic acid, diaspirin, and mixtures thereof.

According to a preferred embodiment, the formulation comprises a form containing the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, said form being provided with a coating for delaying the start of the release of the antidepressant agent with respect to the release of at least 50% by weight (advantageously at least 75% by weight, preferably at least 85% by weight) of the compound selected from the group consisting of acetylsalicylic acid, salts and esters of acetylsalicylic acid, diaspirin, and mixtures thereof. Advantageously, the form is provided with a coating for delaying from 3 minutes to 60 minutes, preferably from 5 minutes to 45 minutes, most preferably from 7 minutes to 30 minutes the start of the release of the antidepressant agent with respect to the release of at least 50% by weight (advantageously at least 75% by weight, preferably at least 85% by weight) of the compound selected from the group consisting of acetylsalicylic acid, salts and esters of acetylsalicylic acid, diaspirin, and mixtures thereof.

The invention relates also to a method of treatment of a patient suffering a depression (especially patient known as resistant to SSRI at a dose of 20 mg for a patient weight of 70 kg or not responding to SSRI at a dose of 20 mg for a patient dose of 70 kg), in which the patient is administered an effective antidepressant amount of one or more pharmaceutically acceptable antidepressant active agents selected from the group consisting of SSRIs selective serotonin reuptake inhibitors, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, such as mixtures of one or more selective serotonin reuptake inhibitors with one or more CRF (corticotropic releasing factor) antagonists and/or NK1 (neurokinin) antagonists and/or NK2 (neurokinin) antagonists and/or NK3 (neurokinin) antagonists, and an effective amount of at least an additive compound selected from the group consisting of acetylsalicylic acid, salts and esters of acetylsalicylic acid, diaspirin, and mixtures thereof, for reducing the onset time of antidepressant action of the pharmaceutically acceptable antidepressant agent selected from the group consisting of SSRIs (selective serotonin reuptake inhibitors), SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. The amount of additive (acetylsalicylic acid, salts and esters of acetylsalicylic acid, diaspirin, and mixtures thereof) is lower than 50 mg for a human with a weight of 70 kg, preferably comprised between 5 mg and 40 mg.

In said method, a formulation of the invention is preferably used. However, the method of the invention can be carried out by other means. For example, the pharmaceutically acceptable antidepressant active agents selected from the group consisting of SSRIs (selective serotonin reuptake inhibitors), SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof and the additive compound are administered successively, preferably first the additive is administered and then the pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof. The pharmaceutically acceptable antidepressant active agents selected from the group consisting of SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof and the additive can be administered by different way, for example the pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof orally, while the additive through the skin or subcutaneous injection (for example in a vein).

In the method of the invention, the doses of pharmaceutically acceptable antidepressant active agents advantageously selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof to be administered to the patient are for example the doses proposed in the commercial formulation of pharmaceutically acceptable antidepressant active agents selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof or by the doctors with such commercial formulation. However, these doses can possibly be lowered, for example by a factor 2 or 3. As it seems also that the time of action (or time efficiency) of the pharmaceutically acceptable antidepressant active agents advantageously selected from the group consisting of SSRIs, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof is increased by the additive, less doses have to be taken with respect to the commercial formulations. For example one daily dose with the formulation of the invention is sufficient, while two or more doses were required for a commercial SSRI formulation, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof.

When using oral dosage form in the system, formulation or methods of the invention, it seems to be advantageous to release the compound selected from the group consisting of ASA, salts thereof, esters thereof, diaspirin and mixtures thereof prior to the release of the antidepressant agent. It seems preferable that the compound selected from the group consisting of ASA, salts thereof, esters thereof, diaspirin and mixtures thereof is released (preferably substantially completely) from 3 minutes to 60 minutes (advantageously from 5 minutes to 45 minutes, preferably from 7 minutes to 30 minutes) prior to the release of the antidepressant agent. For controlling the release of one compound with respect to the other compound, the antidepressant compound is placed in a form, solid form provided with a control means, such as an outer coating or barrier, such as a thick polyacrylate layer, while the ASA is in a quick release form.

The delayed release of the antidepressant agent with respect to the release of the compound selected from the group consisting of ASA, salts and esters thereof, diaspirin, and mixtures thereof can be determined by placing the oral combined form in an aqueous medium having a pH of 1.2 (900 ml), said medium maintained at 37° C. being agitated with paddles apparatus at 100 rpm. The release of the antidepressant agent can be determined and compared with respect to the release of the compound selected from the group consisting of ASA, salts and esters thereof, diaspirin, and mixtures thereof. The start of the release of the antidepressant agent is considered as being as the moment when 5% by weight of the antidepressant agent is released in the medium.

The delayed action or time can also be determined by separating the antidepressant agent (for example in the form of coated beads) from the compound selected from the group consisting of ASA, salts and esters thereof, diaspirin, and mixtures thereof. The antidepressant form free of the compound selected from the group consisting of ASA, salts and esters thereof, diaspirin, and mixtures thereof is tested in order to determine the time T1 required for achieving a 5% by weight release. The compound selected from the group consisting of ASA, salts and esters thereof, diaspirin, and mixtures thereof is tested in order to determine the moment or time T2, T2', and T2" when 50% by weight, 75% by weight and 85% by weight is released. By making the difference between T1 and respectively T2, T2' and T2", it is possible to determine the delayed time of the antidepressant with respect to the release of respectively 50%, 75% and 85% of the compound selected from the group consisting of ASA, salts and esters thereof, diaspirin, and mixtures thereof.

In the method of the invention, the start of the release of the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, is advantageously delayed from 3 minutes to 60 minutes (preferably from 5 minutes to 45 minutes, most preferably from 7 minutes to 30 minutes) with respect to the release of at least 50% by weight (advantageously at least 75% by weight, preferably at least 85% by weight) of the effective amount of the compound selected from the group consisting of acetylsalicylic acid, salts and esters of acetylsalicylic acid, diaspirin, and mixtures thereof.

According to a further embodiment of the method of the invention, the pharmaceutically acceptable antidepressant active agent selected from the group consisting of SSRI agents, SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, is administered from 1 minute to 60 minutes (advantageously from 3 minutes to 60 minutes, preferably from 5 minutes to 45 minutes) after the administration of the effective amount of the compound selected from the group consisting of acetylsalicylic acid, salts and esters of acetylsalicylic acid, diaspirin, and mixtures thereof.

The pharmaceutically acceptable antidepressant active agents selected from the group consisting of SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof are advantageously compounds as disclosed in the following references: for SNRIs (serotonin noradrenaline reuptake inhibitors), CRF (corticotropic releasing factor) antagonists: U.S. Pat. No. 6,525,067; U.S. Pat. No. 6,432,989; U.S. Pat. No. 6,613,777; U.S. Pat. No. 6,610,678; U.S. Pat. No. 6,589,958; U.S. Pat. No. 6,589,952; U.S. Pat. No. 6,469,166 for NK1 (neurokinin) antagonists: U.S. Pat. No. 6,635,630, U.S. Pat. No. 6,096,766 for NK2 (neurokinin) antagonists: U.S. Pat. No. 5,889,024; U.S. Pat. No. 6,444,809, U.S. Pat. No. 6,355,695, U.S. Pat. No. 6,124,279; U.S. Pat. No. 6,008,223; U.S. Pat. No. 5,977,135; U.S. Pat. No. 5,567,700; U.S. Pat. No. 5,521,199 for NK3 (neurokinin) antagonists: U.S. Pat. No. 6,040,316; U.S. Pat. No. 6,602,886; U.S. Pat. No. 6,348,330; U.S. Pat. No. 6,258,943 for combination of NK1 (neurokinin) antagonist with NK2 antagonist: U.S. Pat. No. 6,177,450, U.S. Pat. No. 6,147,083

Examples of SNRIs are commercial products such as Venlafaxine, duloxetine, milnacipram, reboxetine, etc., and mixtures thereof.

DESCRIPTION OF EXAMPLES

Example 1

A PROZAC solid form containing 20 mg fluoxetine was coated with a thin water insoluble barrier coating. The so coated solid form was then coated with a water soluble polymer mixed with ASA (acetyl salicylic acid). The water soluble outer coating comprised about 5 mg ASA.

Examples 2 to 5

Example 1 was repeated except that the amount of ASA in the outer coating was respectively 10 mg, 20 mg, 40 mg.

Examples 6 to 10

Examples 1 to 5 were repeated but with a 10 mg fluoxetine solid form.

Example 11

A solid form containing 35 mg ASA was prepared.
The form was coated with a (water insoluble) barrier coating. The so coated form was then overcoated with a layer (made of a water soluble polymer) in which 10 mg fluoxetine is dispersed. An outer protective layer is advantageously added.

Example 12

Example 11 is repeated except that the fluoxetine containing layer contains 20 mg fluoxetine.

Examples 11 and 12 have been repeated, except that the central ASA solid form contained respectively 10 mg, 20 mg, 40 mg ASA.

It is obvious that the above formulation can be prepared by any techniques, such as spheronisation, so as to prepare microgranules or microspheres of fluoxetine coated with ASA containing layer or microgranules or microspheres of ASA coated with fluoxetine containing layer, with or without intermediate barrier layer.

Examples 1 to 12 have been repeated, except that fluoxetine was replaced by sertraline, paroxetine, citalopram, escitalopram or the s isomer of citalopram, and fluvoxamine.

Example 13

A citalopram solid form containing 20 mg citalopram was coated with a thin water insoluble barrier coating. The so coated solid form was then coated with a water soluble polymer mixed with ASA. The water soluble outer coating comprised about 5 mg ASA.

Examples 14 to 17

Example 13 was repeated except that the amount of ASA in the outer coating was respectively 10 mg, 20 mg, 30 mg and 40 mg.

Example 18

A solid form containing 35 mg ASA was prepared.
The form was coated with a (water insoluble) barrier coating. The so coated form was then overcoated with a layer (made of a water soluble polymer) in which 20 mg citalopram is dispersed. An outer protective layer is advantageously added.

Example 19

Example 18 was repeated except that the solid form contains 25 mg ASA.

Example 20

A solid form containing 10 mg escitalopram was coated with a thin water insoluble barrier coating. The so coated solid form was then coated with a water soluble polymer mixed with ASA. The water soluble outer coating comprised about 5 mg ASA.

Examples 21 to 24

Example 20 was repeated except that the amount of ASA in the outer coating was respectively 10 mg, 20 mg, 35 mg and 40 mg.

Example 25

A solid form containing 35 mg ASA was prepared.

The form was coated with a (water insoluble) barrier coating. The so coated form was then overcoated with a layer (made of a water soluble polymer) in which 10 mg escitalopram is dispersed. An outer protective layer is advantageously added.

Example 26

Example 25 was repeated except that the solid form contains 25 mg ASA.

Examples 27 to 38

Examples 1 to 12 have been repeated except that fluoxetine was replaced by Venlafaxin.

Examples 39 to 74

Examples 1 to 12 have been repeated except that fluoxetine was replaced respectively by Duloxetine, milnacipram and reboxetine.

Example 75

A capsule (hard gelatin) was filled with first solid forms (such as granules) containing fluoxetine and second solid forms (such as granules) containing ASA. The first solid forms correspond to a dose of 20 mg fluoxetine, while the second solid forms correspond to a dose of 20 mg of ASA, The first solid forms comprises an outer barrier layer for protecting the fluoxetine from the ASA.

Examples 76 to 80

Example 75 has been repeated, except that fluoxetine was replaced respectively by Citalopram, escitalopram, Duloxetine, milnacipram and reboxetine

Example 81

A kit is formed with a capsule or tablet containing 20 mg fluoxetine and another capsule or tablet containing 20 mg ASA. The capsules or tablets re advantageously placed in a blister.

Examples 82 to 86

Example 81 has been repeated except that fluoxetine has been replaced respectively by citalopram, escitalopram, duloxetine, milnacipram and reboxetine.

Tests Made on Rats

Four groups of rats have been stressed. One group of rats remain unstressed so as to serve as control.

After being stressed, the rats of the first group received a dose of 50 mg ASA per kg. The second group of rats received no treatment. The third group of rats received 5 mg fluoxetine per kg, and the fourth group of rats received simultaneously 5 mg fluoxetine+50 mg ASA per kg. The treatment was continued during 3 weeks.

The control group of rats had an activity level of 30, while the stressed rats had an activity of 2.

The result of this animal test is after 1 week of treatment with the combination fluoxetine+ASA, the fourth group of rats had an activity of 30, i.e. corresponding to the activity of the unstressed rats or control rats. After 1 week of treatment with ASA or fluoxetine alone, there was no increase at all of the activity.

after three weeks of treatment, the fourth group of rats had still an activity of 30. The third group of rats (treated with fluoxetine) had after 3 weeks an activity of about 25, while no improvement of activity was observed with ASA.

In said test, the doses of ASA and fluoxetine have been adapted for rats.

Said test shows clearly the unexpected action or synergistic activity of ASA+fluoxetine. While not being bound to any theory, it is believed that ASA promotes or activates the sites on which the fluoxetine has to bind.

Further tests have been carried out with lower doses of ASA, namely 25 mg. Similar onset time of antidepressant action was observed.

In view of the reducing time of onset of antidepressant action obtained for the family of SSRI antidepressant, it can be concluded that ASA at dose lower than 50 mg is also efficient for reducing the time of antidepressant onset action for pharmaceutically acceptable antidepressant active agents selected from the group consisting of SNRIs (serotonin noradrenaline reuptake inhibitors), CRF (corticotropic releasing factor) antagonists, NK1 (neurokinin) antagonists, NK2 (neurokinin) antagonists, NK3 (neurokinin) antagonists and combinations thereof, possibly mixed with one or more SSRI.

From said tests and informal tests made on volunteers, in which after (just after, less than 5 minutes after) and prior oral administration of an antidepressant, a dose of ASA was orally administered, it appears that the oral dose of ASA had to be lowered to less than 50 mg, especially between 5 and 50 mg.

At such a low dose of ASA, no bleeding was observed, but a very quick onset of antidepressant action was observed. From this test, it seems that the antidepressant action could already be achieved in less than 7 days, and even in less than 3 to 4 days, although when not using low dose of ASA, the antidepressant action is for example of at least 4 weeks for SSRI.

A comparative test was made on rats by combining a COX II inhibitor with a SSRI (fluoxetine). After 1 week treatment, an antidepressant action could be seen, the efficiency of said combination being however less than 50% of the efficiency of the combination ASA+fluoxetine.

Higher dose of ASA (dose of 100 mg for example) administered to SSRI responding human seems to have no influence or even to have a negative influence on the time of onset of antidepressant action on some SSRI responding patients.

Tests made on SSRI resistant patients or SSRI not responding patients have shown that the combination of the invention, possibly with higher dose of ASA, was suitable for rendering more than 50% of said patients responding quickly to SSRI.

What we claim is:

1. Method of treatment of a human suffering depression, in which the patient is daily administered (a) an effective antidepressant amount from 4 mg to 20 mg of Fluoxetine as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of the antidepressant action of the pharmaceutically acceptable antidepressant active fluoxetine.

2. The method of claim 1, in which the patient is daily administered an oral dosage formulation comprising (a) the effective antidepressant amount from 4 mg to 20 mg of fluoxetine, and (b) an effective amount comprising between 5 and 40 mg of a compound selected from the group consisting of acetylsalicylic acid, salts and esters of acetylsalicylic acid, diaspirin, and mixtures thereof.

3. The method of claim 1, in which the patient is daily administered an oral dosage formulation comprising (a) the effective antidepressant amount from 4 mg to 20 mg of fluoxetine, and (b) an effective amount comprising between 5 and 35 mg of a compound selected from the group consisting of acetylsalicylic acid, salts and esters of acetylsalicylic acid, diaspirin, and mixtures thereof.

4. The method of claim 1, in which the patient is a patient not responding to the sole administration of an effective antidepressant amount of fluoxetine.

5. Method of treatment of a human suffering depression and not responding to the sole administration of fluoxetine, in which the patient is daily administered an effective antidepressant amount from 4 mg to 20 mg of fluoxetine, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of fluoxetine.

6. The method of claim 5, in which the patient is daily administered an oral dosage formulation comprising (a) the effective antidepressant amount from 4 mg to 20 mg of fluoxetine, and (b) an effective amount comprising between 5 and 40 mg of a compound selected from the group consisting of acetylsalicylic acid, salts and esters of acetylsalicylic acid, diaspirin, and mixtures thereof.

7. The method of claim 5, in which the patient is daily administered an oral dosage formulation comprising (a) the effective antidepressant amount from 4 mg to 20 mg of fluoxetine, and (b) an effective amount comprising between 5 and 35 mg of a compound selected from the group consisting of acetylsalicylic acid, salts and esters of acetylsalicylic acid, diaspirin, and mixtures thereof.

8. Method of treatment of a human suffering depression and not responding to the sole administration of an effective antidepressant amount of fluoxetine, in which the patient is daily administered an oral dosage formulation comprising an effective antidepressant amount from 4 mg to 20 mg of fluoxetine as pharmaceutically acceptable antidepressant active agent, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of fluoxetine, in which the oral dosage formulation comprises a control means for delaying after administration of the oral dosage formulation to the patient the start of release of fluoxetine, with a delay from 3 minutes to 60 minutes with respect to the release from said oral dosage formulation after its administration to the patient of at least 50% by weight of the effective amount of the compound selected from the group consisting of acetylsalicylic acid, salts and esters of acetylsalicylic acid, diaspirin, and mixtures thereof, after administration to the patient of said oral dosage formulation.

9. The method of claim 5, in which the pharmaceutically acceptable antidepressant active fluoxetine is orally administered to the patient from 1 minute to 60 minutes after the effective amount of the compound selected from the group consisting of acetylsalicylic acid, salts and esters of acetylsalicylic acid, diaspirin, and mixtures thereof being orally administered to the patient.

10. Method of treatment of a human suffering depression and resistant to the sole administration of an effective antidepressant amount of fluoxetine, in which the patient is daily administered with an oral antidepressant formulation comprising (a) an effective antidepressant amount from 4 mg to 20 mg of fluoxetine, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of fluoxetine.

11. The method of claim 10, in which the oral antidepressant formulation comprising an effective amount comprising between 5 and 40 mg of a compound selected from the group consisting of acetylsalicylic acid, salts and esters of acetylsalicylic acid, diaspirin, and mixtures thereof, is administered.

12. The method of claim 10, in which the oral antidepressant formulation comprising an effective amount comprising between 5 and 35 mg of a compound selected from the group consisting of acetylsalicylic acid, salts and esters of acetylsalicylic acid, diaspirin, and mixtures thereof, is administered.

13. Method of treatment of a human suffering depression and resistant to the sole administration of an effective antidepressant amount of fluoxetine, in which the patient is daily administered with an oral antidepressant formulation comprising (a) an effective antidepressant amount from 4 mg to 20 mg of fluoxetine as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of fluoxetine, in which the oral antidepressant formulation comprises control means whereby the compound selected from the group consisting of acetylsalicylic acid, salts and esters of acetylsalicylic acid, diaspirin, and mixtures thereof is released in the patient after the administration of the oral antidepressant formulation, while the pharmaceutically acceptable antidepressant active fluoxetine is released after the administration of the oral antidepressant formulation to the patient, with a delay from 3 minutes to 60 minutes with respect to the release of at least 50% by weight of the effective amount of the compound selected from the group consisting of acetylsalicylic acid, salts and esters of acetylsalicylic acid, diaspirin, and mixtures thereof, after the administration of the oral antidepressant formulation to the patient.

14. The method of claim 10, in which fluoxetine is released from the oral antidepressant formulation in the patient from 1 minute to 60 minutes after the effective amount of the compound selected from the group consisting of acetylsalicylic acid, salts and esters of acetylsalicylic acid, diaspirin, and mixtures thereof is released from the oral antidepressant formulation in the patient.

15. Method of treatment of a human suffering depression, in which the patient is daily administered (a) an effective antidepressant amount from 4 mg to 20 mg of Citalopram as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of the antidepressant action of the pharmaceutically acceptable antidepressant active citalopram.

16. The method of claim 15, in which the patient is daily administered an oral dosage formulation comprising (a) the effective antidepressant amount from 4 mg to 20 mg of citalopram, and (b) an effective amount comprised between 5 and 40 mg of a compound selected from the group consisting of acetylsalicylic acid, salts and esters of acetylsalicylic acid, diaspirin, and mixtures thereof.

17. The method of claim 15, in which the patient is daily administered an oral dosage formulation comprising (a) the effective antidepressant amount from 4 mg to 20 mg of citalopram, and (b) effective amount comprised between 5 and 35 mg of a compound selected from the group consisting of acetylsalicylic acid, salts and esters of acetylsalicylic acid, diaspirin, and mixtures thereof.

18. The method of claim 15, in which the patient is a patient not responding to the sole administration of an effective antidepressant amount of citalopram.

19. The method of claim 15, in which citalopram is escitalopram.

20. Method of treatment of a human suffering a depression and not responding to the sole administration of an effective antidepressant amount of citalopram, in which the patient is daily administered an effective antidepressant amount from 4 mg to 20 mg of citalopram, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of citalopram.

21. The method of claim 20, in which the patient is daily administered an oral dosage formulation comprising (a) the effective antidepressant amount from 4 mg to 20 mg of citalopram, and (b) an effective amount comprised between 5 and 40 mg of a compound selected from the group consisting of acetylsalicylic acid, salts and esters of acetylsalicylic acid, diaspirin, and mixtures thereof.

22. The method of claim 20, in which the patient is daily administered an oral dosage formulation comprising (a) the effective antidepressant amount from 4 mg to 20 mg of citalopram, and (b) an effective amount comprised between 5 and 35 mg of a compound selected from the group consisting of acetylsalicylic acid, salts and esters of acetylsalicylic acid, diaspirin, and mixtures thereof.

23. The method of claim 20, in which citalopram is escitalopram.

24. Method of treatment of a human suffering depression and not responding to the sole administration of an effective antidepressant amount of citalopram, in which the patient is daily administered an oral dosage formulation comprising an effective antidepressant amount from 4 mg to 20 mg of citalopram as pharmaceutically acceptable antidepressant active agent, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of citalopram,
in which the oral dosage formulation comprises a control means, for delaying after administration of the oral dosage formulation to the patient the start of release of citalopram, with a delay from 3 minutes to 60 minutes with respect to the release from said oral dosage formulation after its administration to the patient of at least 50% by weight of the effective amount of the compound selected from the group consisting of acetylsalicylic acid, salts and esters of acetylsalicylic acid, diaspirin, and mixtures thereof, after administration to the patient of said oral dosage formulation.

25. The method of claim 23, in which citalopram is escitalopram.

26. The method of claim 20, in which the pharmaceutically acceptable antidepressant active citalopram is orally administered to the patient from 1 minute to 60 minutes after the effective amount of the compound selected from the group consisting of acetylsalicylic acid, salts and esters of acetylsalicylic acid, diaspirin, and mixtures thereof being orally administered to the patient.

27. Method of treatment of a human suffering depression and resistant to the sole administration of an effective antidepressant amount of citalopram, in which the patient is daily administered with an oral antidepressant formulation comprising (a) an effective antidepressant amount from 4 mg to 20 mg of citalopram, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of citalopram.

28. The method of claim 27, in which the oral antidepressant formulation comprising an effective amount comprised between 5 and 40 mg of a compound selected from the group consisting of acetylsalicylic acid, salts and esters of acetylsalicylic acid, diaspirin, and mixtures thereof, is administered.

29. The method of claim 27, in which the oral antidepressant formulation comprising an effective amount comprised between 5 and 35 mg of a compound selected from the group consisting of acetylsalicylic acid, salts and esters of acetylsalicylic acid, diaspirin, and mixtures thereof, is administered.

30. Method of treatment of a human suffering depression and resistant to the sole administration of an effective antidepressant amount of citalopram, in which the patient is daily administered with an oral antidepressant formulation comprising (a) an effective antidepressant amount from 4 mg to 20 mg of citalopram as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of citalopram,
in which the oral antidepressant formulation comprises control means whereby the compound selected from the group consisting of acetylsalicylic acid, salts and esters of acetylsalicylic acid, diaspirin, and mixtures thereof is released in the patient after the administration of the oral antidepressant formulation, while the pharmaceutically acceptable antidepressant active citalopram is released after the administration of the oral antidepressant formulation to the patient, with a delay from 3 minutes to 60 minutes with respect to the release of at least 50% by weight of the effective amount of the compound selected from the group consisting of acetylsalicylic acid, salts and esters of acetylsalicylic acid, diaspirin, and mixtures thereof, after the administration of the oral antidepressant formulation to the patient.

31. The method of claim 30, in which citalopram is escitalopram.

32. The method of claim 27, in which citalopram is released from the oral antidepressant formulation in the patient from 1 minute to 60 minutes after the effective amount of the compound selected from the group consisting of acetylsalicylic acid, salts and esters of acetylsalicylic acid, diaspirin, and mixtures thereof is released from the oral antidepressant formulation in the patient.

33. Method of treatment of a human suffering depression, in which the patient is daily administered (a) an effective antidepressant amount from 4 mg to 20 mg of Sertraline as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of the antidepressant action of the pharmaceutically acceptable antidepressant active sertraline.

34. The method of claim 33, in which the patient is daily administered an oral dosage formulation comprising (a) the effective antidepressant amount from 4 mg to 20 mg of sertraline, and (b) an effective amount comprised between 5 and 40 mg of a compound selected from the group consisting of acetylsalicylic acid, salts and esters of acetylsalicylic acid, diaspirin, and mixtures thereof.

35. The method of claim 33, in which the patient is daily administered an oral dosage formulation comprising (a) the effective antidepressant amount from 4 mg to 20 mg of sertraline, and (b) effective amount comprised between 5 and 35 mg of a compound selected from the group consisting of acetylsalicylic acid, salts and esters of acetylsalicylic acid, diaspirin, and mixtures thereof.

36. The method of claim 33, in which the patient is a patient not responding to the sole administration of an effective antidepressant amount of sertraline.

37. Method of treatment of a human suffering a depression and not responding to the sole administration of an effective antidepressant amount of sertraline, in which the patient is daily administered an effective antidepressant amount from 4 mg to 20 mg of sertraline, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of sertraline.

38. The method of claim 37, in which the patient is daily administered an oral dosage formulation comprising (a) the effective antidepressant amount from 4 mg to 20 mg of sertraline, and (b) an effective amount comprised between 5 and 40 mg of a compound selected from the group consisting of acetylsalicylic acid, salts and esters of acetylsalicylic acid, diaspirin, and mixtures thereof.

39. The method of claim 37, in which the patient is daily administered an oral dosage formulation comprising (a) the effective antidepressant amount from 4 mg to 20 mg of sertraline, and (b) an effective amount comprised between 5 and 35 mg of a compound selected from the group consisting of acetylsalicylic acid, salts and esters of acetylsalicylic acid, diaspirin, and mixtures thereof.

40. Method of treatment of a human suffering depression and not responding to the sole administration of an effective antidepressant amount of sertraline, in which the patient is daily administered an oral dosage formulation comprising an effective antidepressant amount from 4 mg to 20 mg of sertraline as pharmaceutically acceptable antidepressant active agent, and an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of sertraline, in which the oral dosage formulation comprises a control means, for delaying after administration of the oral dosage formulation to the patient the start of release of sertraline, with a delay from 3 minutes to 60 minutes with respect to the release from said oral dosage formulation after its administration to the patient of at least 50% by weight of the effective amount of the compound selected from the group consisting of acetylsalicylic acid, salts and esters of acetylsalicylic acid, diaspirin, and mixtures thereof, after administration to the patient of said oral dosage formulation.

41. The method of claim 37, in which the pharmaceutically acceptable antidepressant active sertraline is orally administered to the patient from 1 minute to 60 minutes after the effective amount of the compound selected from the group consisting of acetylsalicylic acid, salts and esters of acetylsalicylic acid, diaspirin, and mixtures thereof being orally administered to the patient.

42. Method of treatment of a human suffering depression and resistant to the sole administration of an effective antidepressant amount of sertraline, in which the patient is daily administered with an oral antidepressant formulation comprising (a) an effective antidepressant amount from 4 mg to 20 mg of sertraline, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of sertraline.

43. The method of claim 42, in which the oral antidepressant formulation comprising an effective amount comprised between 5 and 40 mg of a compound selected from the group consisting of acetylsalicylic acid, salts and esters of acetylsalicylic acid, diaspirin, and mixtures thereof, is administered.

44. The method of claim 42, in which the oral antidepressant formulation comprising an effective amount comprised between 5 and 35 mg of a compound selected from the group consisting of acetylsalicylic acid, salts and esters of acetylsalicylic acid, diaspirin, and mixtures thereof, is administered.

45. Method of treatment of a human suffering depression and resistant to the sole administration of an effective antidepressant amount of sertraline, in which the patient is daily administered with an oral antidepressant formulation comprising (a) an effective antidepressant amount from 4 mg to 20 mg of sertraline as pharmaceutically acceptable antidepressant active agent, and (b) an effective amount between 5 mg and 50 mg of at least a compound selected from the group consisting of acetylsalicylic acid, salts and esters of acetylsalicylic acid, diaspirin, and mixtures thereof, for reducing the time of onset of antidepressant action of sertraline, in which the oral antidepressant formulation comprises control means whereby the compound selected from the group consisting of acetylsalicylic acid, salts and esters of acetylsalicylic acid, diaspirin, and mixtures thereof is released in the patient after the administration of the oral antidepressant formulation, while the pharmaceutically acceptable antidepressant active sertraline is released after the administration of the oral antidepressant formulation to the patient, with a delay from 3 minutes to 60 minutes with respect to the release of at least 50% by weight of the effective amount of the compound selected from the group consisting of acetylsalicylic acid, salts and esters of acetylsalicylic acid, diaspirin, and mixtures thereof, after the administration of the oral antidepressant formulation to the patient.

46. The method of claim 42, in which sertraline is released from the oral antidepressant formulation in the patient from 1 minute to 60 minutes after the effective amount of the compound selected from the group consisting of acetylsalicylic acid, salts and esters of acetylsalicylic acid, diaspirin, and mixtures thereof is released from the oral antidepressant formulation in the patient.

* * * * *